United States Patent [19]

Kleemann et al.

[11] Patent Number: 4,551,548

[45] Date of Patent: Nov. 5, 1985

[54] PROCESS FOR THE RECOVERY OF S-(CARBOXYMETHYL)-(R)-CYSTEINE AND S-(CARBOXYMETHYL)-(S)-CYSTEINE

[75] Inventors: Axel Kleemann, Hanau; Jürgen Martens, Alzenau; Horst Weigel, Rodenbach, all of Fed. Rep. of Germany

[73] Assignee: Degussa Aktiengesellschaft, Frankfurt, Fed. Rep. of Germany

[21] Appl. No.: 477,514

[22] Filed: Mar. 21, 1983

[30] Foreign Application Priority Data

Mar. 26, 1982 [DE] Fed. Rep. of Germany ....... 3211127

[51] Int. Cl.$^4$ ............................................. C07B 19/00
[52] U.S. Cl. ..................................... 562/402; 562/557
[58] Field of Search ................................ 562/402, 557

[56] References Cited

FOREIGN PATENT DOCUMENTS 1456627 9/1966 France .

OTHER PUBLICATIONS

Armstrong. J. Organic Chem., vol. 16, (1951), pp. 749-753.

Angew. Chem., vol. 93 (1981) pp. 680 and 683.

*Primary Examiner*—Natalie Trousof
*Assistant Examiner*—Vera C. Clarke
*Attorney, Agent, or Firm*—Cushman, Darby & Cushman

[57] ABSTRACT

The subject matter of the invention is a process for the recovery of S-(carboxymethyl)-(R)-cysteine and S-(carboxymethyl)-(S)-cysteine from a mixture of the two enantiomers. The mixture to be separated is dissolved in water in the presence of sufficient ammonia that the ammonium salt solution formed has a pH between 6 and 9. Then there is brought about in the solution of ammonium salt a state of supersaturation by the addition of seeding crystals of the ammonium salt of one of the two enantiomers, insofar as the starting material contains one of the two enantiomers in excess, the ammonium salt of this enantiomer, the ammonium salt of one of the two enantiomers is brought to crystallization and separated off. Subsequently by addition of seeding crystals of the ammonium salt of the other enantiomers to the remaining mother liquor the ammonium salt of this enantiomer is likewise brought to crystallization and separated off. Finally the respective S-(carboxymethyl)-cysteine is set free from the two ammonium salts.

15 Claims, No Drawings

PROCESS FOR THE RECOVERY OF S-(CARBOXYMETHYL)-(R)-CYSTEINE AND S-(CARBOXYMETHYL)-(S)-CYSTEINE

BACKGROUND OF THE INVENTION

The subject matter of the invention is a process for the recovery of S-(carboxymethyl)-(R)-cysteine and S-(carboxymethyl-(S)-cysteine from a mixture of the two enantiomers.

S-(carboxymethyl)-cysteine, especially the (R)-enantiomer, has significance as a pharmaceutically active material and is also employed in the cosmetic industry, for example, in the production of hair setting lotions.

For a long time S-(carboxymethyl)-(R)-cysteine was obtained from natural keratin containing raw materials. These raw materials were hydrolyzed and worked up to (R)-cysteine which then subsequently according to the process known from Armstrong, J. Org. Chem. Vol. 16 (1951), pages 749 to 753 could be reacted in alkaline medium with chloroacetic acid to form S-(carboxymethyl)-(R)-cysteine. However, suitable natural raw materials are only available to a limited extent.

In the meantime, however synthetic (RS)-cysteine has become readily accessible, for example, according to the known process from Angew. Chem. Vol. 93 (1981), pages 680 and 683 by way of 2,2-dimethyl-3-thiazoline and 2,2-dimethylthiazolidine-4-carbonitrile. Its reaction with chloroacetic acid then furnishes S-(carboxymethyl)-(R,S)-cysteine. There exists a need to separate this racemate into the two optically active enantiomers, by an efficient resolution process.

SUMMARY OF THE INVENTION

The process of the invention is characterized by dissolving the mixture of the two enantiomers in water in the presence of sufficient ammonia that the solution of ammonium salts formed has a pH between 6 and 9, there being brought about in the solution of ammonium salt a state of supersaturation, by the addition of seeding crystals of the ammonium salt of one of the two enantiomers, insofar as the starting material contains one of the two enantiomers in excess, the ammonium salt of this enantiomer, the ammonium salt of one of the two enantiomers is brought to crystallization, the deposited crystals, separated off seeding crystals of the ammonium salt of the other enantiomer added to the remaining mother liquor to likewise bring to crystallization the ammonium salt of this other enantiomer, the precipitated crystals are separated off and finally the respective S-(carboxymethyl)-cysteine is set free from the ammonium salts.

To carry out the process of the invention the mixture of S-(carboxymethyl)-(R)-cysteine and S-(carboxymethyl)-(S)-cysteine to be separated is either dissolved in agueous ammonia or suspended in water and brought into solution by gassing with gaseous ammonia. In either case the amount of ammonia is so regulated that the solution of ammonium salts formed has a pH between 6 and 9, preferably between 7 and 8.5. In order to obtain an as highly as possible concentrated solution of ammonium salts from the outset, it can be suitable to carry out the process of solution at an elevated temperature between 25° and 70° C.

Then subsequently in the solution of the ammonium salts there is brought about a condition of supersaturation. This can occur depending on the conditions through concentration or cooling the solution, through addition of an organic solvent miscible with water, especially methanol or ethanol or through a combination of several of these procedures.

Then by addition of seeding crystals of the ammonium salt of one of the two enantiomers there is brought to crystallization the ammonium salt of this enantiomer. If the starting mixture is a true racemate, thus contains the two enantiomers in the ratio 1:1, for seeding there can be used the ammonium salt of S-(carboxymethyl)-(R)-cysteine or S-(carboxymethyl)-(S)-cysteine. On the contrary if the starting mixture already contains one of the two enantiomers in excess then there must be used for the seeding step the ammonium salt of the enantiomer present in excess.

The precipitating crystals are separated off, suitably after standing for awhile. The separation can take place in customary manner, e.g. by filtration, centrifuging or decanting the mother liquor. The crude crystals can subsequently be purified further, for example by recrystallization from aqueous methanol, in a given case, with addition of seeding crystals of the optically pure ammonium salt in question.

After the separation of the ammonium salt of the first enantiomer there is then added to the mother liquor remaining which contains an excess of the ammonium salt of the other enantiomer seeding crystals of the ammonium salt of this other enantiomer, through which the ammonium salt of this other enantiomer likewise can be brought to crystallization. The depositing crystals in return are separated off and in a given case purified further in the manner described above.

It is especially advantageous if after separation of the ammonium salt of the first enantiomer there is added to the remaining mother liquor before the further treatment additional racemic S-(carboxymethyl)-cysteine either in the form of the ammonium salt or with simultaneous or subsequent addition of ammonia in such amounts that the solution formed again has a pH value in the above-mentioned range.

Finally, the S-(carboxymethyl)-cysteine is set free in each case from the two separated and, in a given case, further purified ammonium salts. For example, this can occur by dissolving the ammonium salt in water and adjusting the pH with a mineral acid, e.g. hydrochloric acid, to a pH in the vicinity of the isoelectric point of the S-(carboxymethyl)-cysteine, thus a pH of about 2 to 3. The then precipitating S-(carboxymethyl)-cysteine is separated off and dried. Alternatively thereto the ammonium salt can also be converted to the free S-(carboxymethyl)-cysteine with the help of an ion exchanger.

The process of the invention proceeds especially advantageously if it is carried out in numerous steps according to the following diagram. In this diagram "(RS)—SCC.NH$_3$" indicates the ammonium salt of the racemic S-(carboxymethyl)-cysteine, "(R)—SCC.NH$_3$" the ammonium salt of S-(carboxymethyl)-(R)-cysteine and "(S)—SCC.NH$_3$" the ammonium salt of S-(carboxymethyl-(S)-cysteine.

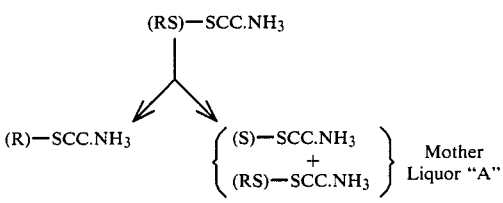

-continued

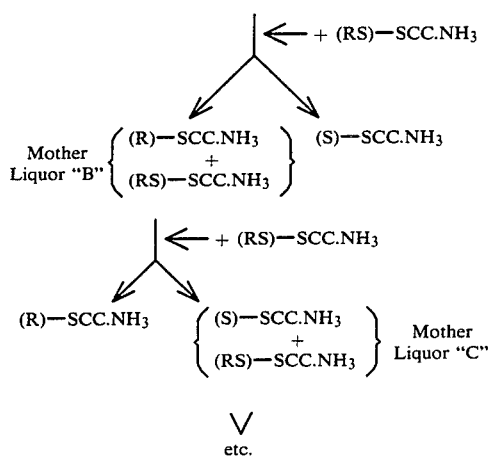

etc.

The recrystallization of the ammonium salt separated off in certain cases, which is sometimes necessary, is not considered in this diagram for better clarity. If a recrystallization is undertaken then suitably the mother liquor resulting thereby is added to an appropriate mother liquor of the separatory process, thus, e.g. adding the mother liquor from the recrystallization of (R)—SCC.NH$_3$ to mother liquor "B" etc. and adding the mother liquor from the recrystallization of (S)—SCC.NH$_3$ to mother liquor "A", "C", etc. Insofar as the condition of supersaturation in the solution of the ammonium salt is brought about by the addition of an organic solvent and/or in the recrystallization of the ammonium salt at times separated off there is concomitant use of such an organic solvent it is recommended before further processing the mother liquors which are combined, in a given case, to separate off the organic solvents.

In the pictured many step process ultimately the ammonium salts of the two enantiomers are completely separated from each other which leads to a correspondingly high yield of the two optically active S-(carboxymethyl)-cysteines.

The process of the invention can also be used in the purification of crude S-(carboxymethyl)-(R)-cysteine or S-(carboxymethyl)-(S)-cysteine still having unsatisfactory optical purity which already contain one of the two enantiomers in excess. This additional purification is of particular significance for the recovery of pure S-(carboxymethyl)-(R)-cysteine which has been produced from (RR)-cystine or (R)-cysteine. In the hydrolysis of natural keratin containing raw materials there occurs to a considerable extent racemization of the natural cystine or cysteine.

On the other hand, naturally the S-(carboxymethyl)-(S)-cysteine, which up to now has no commercial outlet can be subjected to a racemization treatment and then serve as starting material for obtaining further S-(carboxymethyl)-(R)-cysteine. The racemization for example can be effected by boiling in aqueous hydrochloric acid solution in the presence of salicylaldehyde.

The process of the invention can comprise, consist essentially of, or consist of the stated steps with the recited materials.

The invention is explained in more detail in the following examples. Unless otherwise indicated, all parts and percentages are by weight.

DETAILED DESCRIPTION

The S-(carboxymethyl)-(RS)-cysteine employed in the examples was produced as follows:

140 grams (1 mole) of synthetic (RS)-cysteine hydrochloride and 160 grams (4 moles) of sodium hydroxide were dissolved in 1000 ml of water. To the solution there were first added 3 grams of sodium bisulfite and then in the course of 45 minutes 95 grams (1 mole) of monochloroacetic acid. The temperature of the reaction mixture meanwhile was held at 20° C. and subsequently held for 3 hours at 25° to 30° C. Finally by addition of concentrated aqueous hydrochloric acid the pH was adjusted to 3.0 whereupon the S-(carboxymethyl)-(RS)-cysteine separated out. It was filtered off at 10° C., washed with water until the filtrate was free from chloride ions and dried under reduced pressure at 150° C. The yield was 173 grams, corresponding to 97% of theory, the melting point was 188° to 192° C. (decomposition).

Elemental Analysis:

|  | C | H | N | S |
|---|---|---|---|---|
| Found: | 33.70% | 5.07% | 7.91% | 17.79% |
| Calculated: | 33.51% | 5.06% | 7.82% | 17.89% |

The optically active enantiomers obtained in the examples were in each case examined as to their specific rotation $[\alpha]_D^{20}$ in degrees.cm$^3$/dm.g.

EXAMPLE 1

40 grams of S-(carboxymethyl)-(RS)-cysteine were mixed with 40 ml of water and treated under heating to 60° C. with 24% aqueous ammonia solution until a clear solution formed at pH 8.5. After addition of 70 ml of methyl alcohol the mixture was cooled to 20° C. and seeded with 220 mg of the ammonium salt of S-(carboxymethyl)-(R)-cysteine. After 70 minutes the mixture was filtered with suction. After the recrystallization of the residue from 70% aqueous methyl alcohol there were obtained 3.1 grams of the ammonium salt of S-(carboxymethyl)-(R)-cysteine having a degree of rotation $[\alpha]_D^{20} = -29.8$ (c=5, water).

The salt was dissolved in 20 ml of water and a pH of 2.5 established with hydrochloric acid. After filtering with suction, washing with 100 ml of water and drying there remained 2.6 grams of S-(carboxymethyl)-(R)-cysteine having a degree of rotation $[\alpha]_D^{20} = -34.4°$ (c=5, water, aqueous sodium hydroxide to pH 6).

In the filtrate remaining after separating off the ammonium salt of S-(carboxymethyl)-(R)-cysteine after heating to 35° C. there were dissolved 8 grams of the ammonium salt of S-(carboxymethyl)-(RS)-cysteine. The clear solution was cooled to 20° C. and seeded with a few crystals of the ammonium salt of S-(carboxymethyl)-(S)-cysteine. After 35 minutes there were obtained by filtering off with suction 7.8 grams of the ammonium salt of S-(carboxymethyl)-(S)-cysteine having a degree of rotation $[\alpha]_D^{20} = +20.7°$ (c=5, water).

The salt was recrystallized from aqueous methyl alcohol, then dissolved in 20 ml of water. The solution was acidified with hydrochloric acid to pH 2.5. By filtering with suction, washing with 200 ml of water and drying there were obtained 4.8 grams of S-(carboxymethyl)-(S)-cysteine have a degree of rotation $[\alpha]_D^{20} = +34.0°$ (c=5, water, aqueous sodium hydroxide to pH 6).

EXAMPLE 2

A mixture of 75 grams of S-(carboxymethyl)-(RS)-cysteine and 5 grams of S-(carboxymethyl)-(R)-cysteine was dissolved in 70 ml of water and 42 ml of 24% aqueous ammonia solution with heating to 60° C. The clear solution having a pH of 8.0 was treated with 140 ml of methyl alcohol and cooled to 25° C. The supersaturated solution under slow stirring was seeded with 200 mg of the ammonium salt of S-(carboxymethyl)-(R)-cysteine. After 25 minutes the coarse, colorless crystals were filtered off with suction and dried at 50° C. under reduced pressure. There were obtained 19.1 grams of the ammonium salt of S-(carboxymethyl)-(R)-cysteine having a rotary value $[\alpha]_D^{20} = -25.6°$ (c=5, water).

By recrystallization from 80% aqueous methyl alcohol the rotary value increased to $[\alpha]_D^{20} = -30.6°$.

The salt was dissolved in 50 ml of water and the solution acidified with hydrochloric acid to pH 2.5. The crystals which deposited were filtered off with suction, washed with water and dried. There were obtained 13.9 grams of S-(carboxymethyl)-(R)-cysteine having a rotary value $[\alpha]_D^{20} = -35.1°$ (c=5, water, aqueous sodium hydroxide to pH 6).

The filtrate remaining after the separation of the ammonium salt of S-(carboxymethyl)-(R)-cysteine was seeded with 100 mg of the ammonium salt of S-(carboxymethyl)-(S)-cysteine and allowed to stand for 20 minutes. By filtering with suction and drying there were obtained 8.6 grams of the ammonium salt of S-(carboxymethyl)-(S)-cysteine having a degree of rotation $[\alpha]_D^{20} = +24.8°$ (c=5, water).

By recrystallization from 80% aqueous methyl alcohol the degree of rotation increased to $[\alpha]_D^{20} = +30.6°$.

The salt was dissolved in 40 ml of water and the solution acidified with hydrochloric acid to pH 2.5. The crystals which deposited were filtered off with suction, washed with water and dried. There were obtained 6.1 grams of S-(carboxymethyl)-(S)-cysteine having a degree of rotation $[\alpha]_D^{20} = +35.0°$ (c=5, water, aqueous sodium hydroxide to pH 6).

EXAMPLE 3

A mixture of 74 grams of S-(carboxymethyl)-(RS)-cysteine and 6 grams of S-(carboxymethyl)-(S)-cysteine were stirred with heating to 50° C. with 70 ml of water and treated with 24% aqueous ammonia until a clear solution was formed at pH 7.8. After addition of 140 ml of methyl alcohol the solution was cooled to 23° C., seeded with 60 mg of the ammonium salt of S-(carboxymethyl)-(S)-cysteine and allowed to stand for 20 minutes without stirring. By subsequent filtering with suction and drying there were obtained 20.4 grams of the ammonium salt of S-(carboxymethyl)-(S)-cysteine having a degree of rotation $[\alpha]_D^{20} = +23.8°$ (c=5, water).

By recrystallization from 80% aqueous methylalcohol the degree of rotation increased to $[\alpha]_D^{20} = +30.8°$.

Elemental Analysis: $C_5H_{12}N_2O_4S$:

|  | C | H | N | S |
|---|---|---|---|---|
| Found: | 30.48% | 6.21% | 14.10% | 16.30% |
| Calculated: | 30.60% | 6.16% | 14.28% | 16.34% |

The salt was dissolved in 50 ml of water and the solution acidified with hydrochloric acid to pH 2.5. After the filtering with suction, washing with 90 ml of water and drying there were obtained 12.9 grams of S-(carboxymethyl)-(S)-cysteine having a degree of rotation $[\alpha]_D^{20} = +34.8°$ (c=5, water, aqueous sodium hydroxide to pH 6).

The filtrate remaining after separating off the ammonium salt of S-(carboxymethyl)-(S)-cysteine was treated with 20 grams of S-(carboxymethyl)-(RS)-cysteine, heated to 45° C. and converted into a clear solution by leading in gaseous ammonia to pH 7.8. After cooling to 28° C. and seeding the supersaturated solution with 50 mg of the ammonium salt of S-(carboxymethyl)-(R)-cysteine there crystallized out within 25 minutes 19.6 grams of the ammonium salt of S-(carboxymethyl)-(R)-cysteine having a degree of rotation $[\alpha]_D^{20} = -21.6°$ (c=5, water).

After recrystallization from 80% aqueous methyl alcohol the degree of rotation increased to $[\alpha]_D^{20} = +30.1°$.

The salt was dissolved in 50 ml of water and the solution acidified with hydrochloric acid to pH 2.5. By filtering with suction, washing with 40 ml of water and drying there were obtained 13.3 grams of S-(carboxymethyl)-(R)-cysteine having a degree of rotation $[\alpha]_D^{20} = -35.1°$ (c=5, water, aqueous sodium hydroxide to pH 6).

Elemental Analysis:

|  | C | H | N | S |
|---|---|---|---|---|
| Found | 33.65% | 5.12% | 7.94% | 17.82% |
| Calculated: | 33.51% | 5.06% | 7.82% | 17.89% |

EXAMPLE 4

A mixture of 91 grams of S-(carboxymethyl)-(RS)-cysteine and 9 grams of S-(carboxymethyl)-(S)-cysteine were treated in a water bath at 50° C. with 40 ml of water and stirred with concentrated aqueous ammonia solution until a clear solution formed at pH 7.6. This solution was cooled to 25° C. and seeded with 100 mg of the ammonium salt of S-(carboxymethyl)-(S)-cysteine. After 45 minutes the crystal mass was filtered off with suction and there were obtained 23.3 grams of the ammonium salt of S-(carboxymethyl)-(S)-cysteine having a degree of rotation $[\alpha]_D^{20} = +24.2°$ (c=5, water) and the mother liquor "A".

The salt was recrystallized from 80% aqueous methyl alcohol, dissolved in 50 ml of water and the solution acidified with hydrochloric acid to pH 2.5. After filtering with suction, washing with 75 ml of water and drying there were obtained 16.0 grams of S-(carboxymethyl)-(S)-cysteine having a degree of rotation $[\alpha]_D^{20} = +34.8°$ (c=5, water, aqueous sodium hydroxide to pH 6).

The mother liquor "A" was heated to 50° C., treated with 20 grams of S-(carboxymethyl)-(RS)-cysteine and adjusted to pH 7.6 with concentrated aqueous ammonia solution. After cooling to 25° C. the solution was then seeded with 100 mg of the ammonium salt of S-(carboxymethyl)-(R)-cysteine.

After 45 minutes it was filtered with suction again and there were obtained 20.5 grams of the ammonium salt of S-(carboxymethyl)-(R)-cysteine having a degree of rotation $[\alpha]_D^{20} = -23.9°$ (c=5, water) and the mother liquor "B".

The salt was recrystallized from 80% aqueous methyl alcohol, dissolved in 50 ml of water and acidified to pH 2.5 with hydrochloric acid. After filtering with suction, washing with 50 ml of water and drying there were obtained 14.2 grams of S-(carboxymethyl)-(R)-cysteine having a degree of rotation $[\alpha]_D^{20} = -35.0°$ (c=5, water, aqueous sodium hydroxide to pH 6).

The mother liquor "B" was again heated to 50° C., treated with 20 grams of S-(carboxymethyl)-(RS)-cysteine and a pH of 7.6 established with concentrated aqueous ammonia solution. After cooling to 25° C. this time it was again seeded with 100 mg of the ammonium salt of S-(carboxymethyl)-(S)-cysteine. After 45 minutes it was again filtered with suction and there were obtained a further 22.6 grams of the ammonium salt of S-(carboxymethyl)-(S)-cysteine having a degree of rotation $[\alpha]_D^{20} = +23.0°$ (c=5, water) and the mother liquor "C".

The salt was again recrystallized from 80% aqueous methyl alcohol, dissolved in 50 ml of water and the solution acidified with hydrochloric acid to pH 2.5. After filtering with suction, washing with 150 ml of water and drying there were obtained a further 15.5 grams of S-(carboxymethyl)-(S)-cysteine having a degree of rotation $[\alpha]_D^{20} = +35.1°$ (c=5, water, aqueous sodium hydroxide to pH 6).

The procedure with mother liquor "C" was likewise carried out as described above with mother liquor "A" and there were obtained a further 14.5 grams of S-(carboxymethyl)-(R)-cysteine.

The entire disclosure of German priority application No. P3211127.4 is hereby incorporated.

What is claimed is:

1. A process for obtaining purified S-(carboxymethyl)-(R)-cysteine and purified S-(carboxymethyl)-(S)-cysteine from a mixture of the two enantioners comprising dissolving the mixture of the two enantiomers in water in the presence of sufficient ammonia that the solution of ammonium salts formed has a pH between 6 and 9, bringing about in the solution of ammonium salts a state of supersaturation by the addition of seeding crystals of the ammonium salt of one of the two enantiomers, crystallizing one of the two enantiomers, separating off the crystals, adding seeding crystals of the ammonium salt of the other enantiomer to the remaining mother liquor to crystallize the ammonium salt of this other enantiomer, separating off the precipitated crystals and finally setting free from the ammonium salts the respective S-(carboxymethyl)-cysteines.

2. A process according to claim 1 wherein the starting mixture contains an excess of one of the two enantiomers and the first seeding crystal is the ammonium salt of the enantiomer which is in excess whereby the ammonium salt of the enantiomer first crystallized is that of the enantiomer which is in excess.

3. A process according to claim 1 wherein the starting mixture contains both enantiomers in the same amount.

4. A process according to claim 1 wherein the ammonia is added in the form of an aqueous solution.

5. A process according to claim 1 wherein the ammonia is added in gaseous form.

6. A process according to claim 1 including the step of forming the supersaturated solution of the ammonium salts by concentrating a lower concentrated solution of the ammonium salts.

7. A process according to claim 1 including the step of forming the supersaturated solution of the ammonium salts by lowering the temperature of the solution from a temperature level at which the solution is not supersaturated to a temperature at which the solution is supersaturated.

8. A process according to claim 1 including the step of forming the supersaturated solution of the ammonium salts by adding a water miscible organic solvent to a non-saturated solution of the ammonium salts, the ammonium salts having a lower solubility in the organic solvent than in water.

9. A process according to claim 8 including the step after the separation of the ammonium salt of the first enantiomer and before further treatment either (1) adding racemic S-(carboxymethyl)-cysteine and ammonia or (2) adding the ammonium salt of racemic S-(carboxymethyl)-cysteine.

10. A process according to claim 7 including the step after the separation of the ammonium salt of the first enantiomer and before further treatment either (1) adding racemic S-(carboxymethyl)-cysteine and ammonia or (2) adding the ammonium salt of racemic S-(carboxymethyl)-cysteine.

11. A process according to claim 6 including the step after the separation of the ammonium salt of the first enantiomer and before further treatment either (1) adding racemic S-(carboxymethyl)-cysteine and ammonia or (2) adding the ammonium salt of racemic S-(carboxymethyl)-cysteine.

12. A process according to claim 1 including the step after the separation of the ammonium salt of the first enantiomer and before further treatment either (1) adding racemic S-(carboxymethyl)-cysteine and ammonia or (2) adding the ammonium salt of racemic S-(carboxymethyl)-cysteine.

13. A process according to claim 9 wherein there are added racemic S-(carboxymethyl)-cysteine and ammonia after the separation of the ammonium salt of the first enantiomer.

14. A process according to claim 9 wherein there is added the ammonium salt of racemic S-(carboxymethyl)-cysteine after the separation of the ammonium salt of the first enantiomer.

15. A process according to claim 1 wherein the pH of the solution of ammonium salts formed is 7 to 8.5.

* * * * *